(12) United States Patent
Banas et al.

(10) Patent No.: US 12,721,717 B2
(45) Date of Patent: Sep. 1, 2026

(54) ASSEMBLY FOR AORTIC END-TO-SIDE ANASTAMOSIS

(71) Applicant: ConneX BioMedical, Inc., Aurora, CO (US)

(72) Inventors: Christopher E. Banas, Breckenridge, CO (US); Jeffrey N. Steinmetz, Arvada, CO (US); Max Bannister Mitchell, Castle Pines, CO (US)

(73) Assignees: Connex Biomedical, Inc., Aurora, CO (US); The Regents of the University of Colorado, a Body Corporate, Denver, CO (US)

( * ) Notice: Subject to any disclaimer, the term of this patent is extended or adjusted under 35 U.S.C. 154(b) by 456 days.

(21) Appl. No.: 18/188,390

(22) Filed: Mar. 22, 2023

(65) Prior Publication Data

US 2023/0329855 A1 Oct. 19, 2023

Related U.S. Application Data

(60) Provisional application No. 63/323,056, filed on Mar. 23, 2022.

(51) Int. Cl.
*A61F 2/06* (2013.01)
*A61B 17/11* (2006.01)

(52) U.S. Cl.
CPC .............. *A61F 2/064* (2013.01); *A61B 17/11* (2013.01); *A61B 2017/1107* (2013.01); *A61B 2017/1135* (2013.01); *A61F 2220/0016* (2013.01)

(58) Field of Classification Search
CPC ............ A61B 17/11; A61B 2017/1107; A61B 2017/1135; A61B 2002/061; A61F 2/07;
(Continued)

(56) References Cited

U.S. PATENT DOCUMENTS 6,565,581 B1 * 5/2003 Spence .............. A61B 17/1152 606/153
11,123,542 B1 * 9/2021 Mitchell ................ A61B 17/11
(Continued)

FOREIGN PATENT DOCUMENTS

DE 19936120 A1 7/1999
WO WO 9300868 1/1993

OTHER PUBLICATIONS

Written Opinion of the International Searching Authority; International Application No. PCT/US2023/064833. Dated Jun. 16, 2023.
(Continued)

*Primary Examiner* — Diane D Yabut
(74) *Attorney, Agent, or Firm* — Rosenbaum IP, P.C.; David G. Rosenbaum

(57) ABSTRACT

An assembly and method for end-to-side anastomosis to an anatomical conduit is disclosed. The system and method are particularly useful in coupling an LVAD pump to an aorta. The assembly and method include using a tubular graft member having a distal flange section that conforms to and engages an abluminal wall surface of the aorta, an affixation component having a tubular proximal section and a distal flange section that is configured to conform to and engage with a luminal wall surface of the aorta and has a plurality of receiver openings passing through the distal flange section, and a plurality of anchoring components configured to pass through the distal flange section of the graft component, through the wall of the aorta or other major vessel, an engage with the receiver openings of the distal flange section of the affixation component to exert an axially compressive force there between and create a hemostatic seal around an opening formed in the wall of the aorta or major vessel that allows blood or other fluid to pass into and through the assembly and into the aorta or other anatomical conduit.

19 Claims, 7 Drawing Sheets

(58) Field of Classification Search
CPC ........ A61F 2002/061; A61F 2220/0033; A61F 2220/0041; A61M 1/3655
See application file for complete search history.

(56) References Cited

U.S. PATENT DOCUMENTS

| | | | | |
|---|---|---|---|---|
| 2001/0029383 | A1* | 10/2001 | Solem | A61F 2/064 606/153 |
| 2005/0192604 | A1* | 9/2005 | Carson | A61F 2/2493 606/153 |
| 2015/0320424 | A1* | 11/2015 | Gourlay | A61F 2/064 606/153 |
| 2016/0346025 | A1* | 12/2016 | Bonutti | A61L 24/04 |

OTHER PUBLICATIONS

Notification of Transmittal of the International Search Report and the Written Opinion of the International Searching Authority, or the Declaration; International Application No. PCT/US2023/064833. Dated Jun. 16, 2023.

International Search Report; International Application No. PCT/US2023/064833. Dated Jun. 16, 2023.

* cited by examiner

ASSEMBLY FOR AORTIC END-TO-SIDE ANASTAMOSIS

CROSS-REFERENCE TO RELATED APPLICATIONS

This application is related to and claims priority to U.S. provisional patent application Ser. No. 63/323,056, filed Mar. 23, 2022.

BACKGROUND OF THE INVENTION

The present invention pertains generally to devices and methods for joining a tubular conduit to an anatomic passageway, such as, for example, a blood vessel, a lymph duct, a trachea or other airway, an esophagus, stomach, small or large intestine, or the like. More particularly, the present invention relates to an assembly for creating an end-to-side anastomosis between a tubular conduit and a portion of the anatomic passageway, such, for example, the aorta or other major blood vessel. Still more particularly, the present invention pertains to an assembly that generally includes an affixation component, a graft component, and an anchoring component. For purposes of clarity and by way of non-limiting example only, reference to a major blood vessel, such as the aorta, may be made herein as an example of an anatomic passageway into which the assemblies described herein may be deployed.

The affixation component is an expandable stent-like device having a tubular proximal section and a distal section that projects diametrically outward from the tubular proximal section. The distal section is configured to conform to a luminal wall surface of the anatomic passageway and may, optionally, be configured to have or to assume a substantially saddle-shape when delivered. According to one variant of the present disclosure, the distal section is a radially extending flange that projects diametrically outward from a distal aspect of the tubular proximal section along at least radial axis of the tubular proximal section. The distal section of the affixation component has a plurality of receiver openings provided therein, each of which are configured to receive tissue anchors therethrough or therein. The plurality of receiver openings are positioned to engage the tissue anchors and exert an axially compressive force between the graft component, the anatomic tissue of the anatomic passageway, and the affixation component. The plurality of tissue anchors may be arrayed about at least a portion of a circumferential aspect of the distal section of the affixation component. The tubular proximal section is contiguous with the distal section and projects proximally from the distal section and terminates in a proximal opening that is co-axial with the tubular proximal section. The tubular proximal section and the distal section are both diametrically expandable from a first compressed or folded configuration to a second expanded or deployed configuration. In this manner the affixation component is capable of being delivered by a delivery catheter in a minimally invasive procedure.

The graft component is a pliable or semi-pliable tubular graft having a distal flange. The distal flange is also configured to conform to a curvature of an abluminal wall surface of an anatomic passageway. To achieve this conformation, the distal flange of the graft component may be configured to have or assume a substantially saddle-shape. The graft component will also have either indicia marked thereupon or openings to allow for alignment with the receiver openings of the affixation component and for engagement with the anchoring component or tissue anchors.

The anchoring component includes a plurality of tissue anchors and, optionally, one or more compression plates. The plurality of tissue anchors may include tissue screws, pins, retainers, clips, barbs, hooks, or other similar types of engagement members. The optional compression plate(s) are configured to conform to the distal flange of the graft and/or the curvature of the abluminal surface of the aorta. The compression plate(s) may be a single annular member or plural members that seat against an upper surface of the distal flange of the graft component and, under the influence of the tissue anchors, exert an axially compressive force between the graft component and the affixation component. The compression plate(s) have openings that allow the tissue anchors to pass into and through the openings, seat against an outer surface of the compression plate(s), pass into and through the distal flange of the graft component, into and through the aorta, and engage with the receiver openings of the affixation component to draw the affixation component and the graft component together with the aorta there between.

In one example of an application of the end-to-side anastomosis assembly, the assembly has particular application in coupling an outflow conduit of a ventricular assist device ("VAD") such as a left ventricular assist device ("LVAD") to create a blood flow path from the VAD to the aorta. It will be understood that the end-to-side anastomosis assembly has other non-vascular medical applications to anatomic passageways. Additionally, non-medical applications of the devices and methods are also intended and contemplated by the present disclosure. Further, the medical application to VAD or LVAD devices is intended to be a non-limiting example of an application of the devices and methods described herein.

Heart failure is a leading cause of death in developed countries. An estimated 100,000 Americans develop end-stage congestive heart failure each year with a one-year mortality of approximately 50%. There are many etiologies of heart failure. Treatment options depend on the underlying cause and consist of drug therapy, catheter based or surgical interventions for coronary artery disease, and catheter or surgical procedures for valve disease and other lesions. In the past, the only treatment for end-stage non-correctable heart failure was heart transplantation. Approximately 2,000 heart transplant procedures are performed annually in the United States and approximately 5,000 are performed annually world-wide. At any given time, there are approximately 3,000 patients on the heart transplant waiting list in the United States. Consequently, demand for transplantation far outstrips the supply of donor hearts, and it is unlikely that this supply imbalance will improve. Because of the donor supply imbalance, practitioners have developed mechanical VAD systems to support the circulation in patients with heart failure.

Initially, VAD therapy was limited to heart transplant candidates and was intended to bridge patients to heart transplant and improve their baseline health status going into transplant. This strategy is commonly referred to as Bridge to Transplant ("BTT"). As technology improved, VAD outcomes improved and VAD therapy was extended to the larger population of heart failure patients who are not candidates for transplant. VAD treatment in the latter pool of patients is referred to as Destination Treatment ("DT"). Most patients, regardless of treatment intent, can be supported with a left sided device alone.

The current generation of LVADs in common use are continuous flow devices. The newer continuous flow LVADs are small enough to be implanted entirely within the pericardial space and do not require an intra-abdominal pocket. In general, the pumping inlet mechanism of current LVADs is surgically attached directly to a heart chamber. The outflow end of the pumping mechanism consists of a prosthetic vascular tube graft that is sewn end to side to a major artery-usually the aorta. There are other surgical indications for the attachment of the end of a large prosthetic vascular graft to the side of a major artery. For example, aorta to aorta bypass procedures require end-to-side attachment of a prosthetic graft to the aorta at one end and the aorta at the other end. An alternative example of an application for the end-to-side anastomosis system is in implanting an apical-aortic valve conduit in which a valved conduit is implanted into the left ventricular apex and then a distal end of the valved conduit is joined by an end-to-side anastomosis to the aorta bypassing the aortic valve.

VAD pumping devices require a connection to the heart muscle. Typical VAD connectors are apical cuffs that are first attached to the left ventricular apex and support attachment of the LVAD pumping device to the left ventricular apex. To couple the VAD, an apical opening is formed in the ventricular apex central to the apical cuff and the LVAD pumping device is then attached to the apical cuff with a portion of the pumping device passing through the apical opening to communicate with the ventricular chamber. Apical cuffs typically consist of a rigid metal cylinder surrounded by a fabric sewing ring. A device and method for implanting an apical cuff is described in commonly assigned U.S. Pat. No. 10,335,527 issued Jul. 2, 2019, which is hereby incorporated by reference in its entirety as teaching a device and method for apical cuff implantation for attachment of a ventricular assist device.

Conventional methods for the surgical attachment, e.g., anastomosis, of the end of a large prosthetic tube graft to the side of a major artery typically involve isolating a segment of the target artery with a side-biting clamp or between two completely occlusive clamps. An opening is created in the target artery, known as an arteriotomy, and the prosthetic tube graft is manually sutured to the arteriotomy in an end to side manner with the arteriotomy opening and a central lumen of the prosthetic tube graft being in fluid flow communication with each other. Suturing methods vary and include running suture techniques, interrupted suture techniques, i.e., using a plurality of individually placed and tied sutures, or a combination of these methods. Conventional suturing methods are time consuming, require clamping of the target vessel which in some cases may be diseased, and can be associated with suture hole bleeding due to suture hole elongation. In contrast, by eliminating the suturing, the assembly of the present disclosure decreases procedure time, standardizes the procedure so that it is not dependent upon a surgeons technical abilities, and is minimally invasive to reduce the need for surgical access to the site for the end-to-side anastomosis.

While the present invention will be described with respect to its use with a VAD procedure and system, those skilled in the art will understand and appreciate that the scope of the present invention is intended not to be limited to VAD procedures and systems but to end-to-side connections between tubular medical grafts, autologous anatomical tubular grafts, heterologous or other biological tubular grafts, and other anatomical structures, such as the gastrointestinal system, biliary system, lymphatic system, urinary system or the like.

SUMMARY OF THE INVENTION

The currently disclosed devices, assemblies, and method for making an end-to-side connection between a tubular conduit and an anatomic passageway, such as a major blood vessel.

As an example of a use of the disclosed assemblies, there is provided an end-to-side anastomosis assembly configured to be coupled to a circumferential aspect of a blood vessel, such as the aorta, to direct blood flow into the aorta from a remote location in the body. an assembly that generally includes an anchoring component, a graft component, and an affixation component.

The affixation component is an expandable stent-like device having a tubular proximal section and a distal section. The distal section is configured to conform to a curvature of a luminal wall surface of the aorta. To achieve such conformation, the distal section may be configured, such as by heat setting a shape memory material, to assume a substantially saddle-shape. The distal section of the affixation component may, optionally, be comprised of a plurality of radially extending strut members. At least one interconnecting strut may be provided that connects the radially extending strut members. A plurality of receiver openings configured to receive tissue anchors are provided on the distal section, such as in conjunction with the radially extending strut members and/or the interconnecting struts. The plurality of receiver openings are positioned about the distal section of the affixation component and are configured to receive tissue anchors therethrough. The tubular proximal section of the affixation component is contiguous with the distal section that projects outwardly from a distal aspect of the tubular proximal section. The entire affixation component, including the tubular proximal section and the distal section, is diametrically expandable from a compressed or folded configuration. In this manner the affixation component is capable of being delivered by a delivery catheter and diametrically expended once positioned at a delivery site.

Optionally, the affixation component may have a graft integrated with the tubular proximal section and extending toward the intersection with the distal section to facilitate achieving a hemostatic seal with the aorta. In this optional configuration, the integral graft on the tubular proximal section of the affixation component may obviate the need for a separate graft component. An example of an integrated graft with a stent is found at U.S. Pat. No. 5,749,880 which discloses an expanded polytetrafluoroethylene (ePTFE) covering encapsulating a diametrically expandable stent and which is hereby incorporated by reference. Those skilled in the art will understand that there are a wide variety of graft covered stents known in the art and that a wide variety of manners of encapsulating, embedding, joining, coupling, or otherwise covering the luminal and/or abluminal surface of a tubular stent are well known in the art.

The graft component is a pliable or semi-pliable tubular graft having a distal flange. The distal flange is also configured to conform to the abluminal surface curvatures, in both the longitudinal and circumferential axes, of the aorta or anatomical passageway. To achieve such curvature conformation, the distal flange may be sufficiently pliable to conform to such curvatures or may be pre-shaped to conform to such curvatures. In either case, the conformation of the distal flange will assume a generally saddle-shape that conforms to the longitudinal and circumferential curvatures of the abluminal surface of the major vessel or other anatomical passageway.

The graft component may also have orientation or alignment indicia marked thereupon, such as on the distal flange of the graft component to facilitate alignment of with the receiver openings of the affixation component. Alternatively, or in addition, the distal flange of the graft component may have openings configured to align with the receiver openings of the affixation component and through within the anchoring component may pass.

The anchoring component includes a plurality of tissue anchors and, optionally, one or more compression plates. The plurality of tissue anchors may include tissue screws, pins, retainers, clips, or the like. The optional compression plate(s) are configured to conform to the saddle-shape of the distal flange of the graft and the curvature of the abluminal surface of the aorta. The compression plate(s) may be a single annular member or plural members that seat against an upper surface of the distal flange of the graft component and, under the influence of the tissue anchors, exert an axially compressive force between the graft component and the affixation component. The compression plate(s) have openings that allow the tissue anchors to pass into and through the openings, seat against an outer surface of the compression plate(s), pass into and through the distal flange of the graft component, into and through the aorta, and engage with the receiver openings of the affixation component to draw the affixation component and the graft component together with the aorta there between.

DETAILED DESCRIPTION OF THE PREFERRED EMBODIMENTS

Figure 1A:
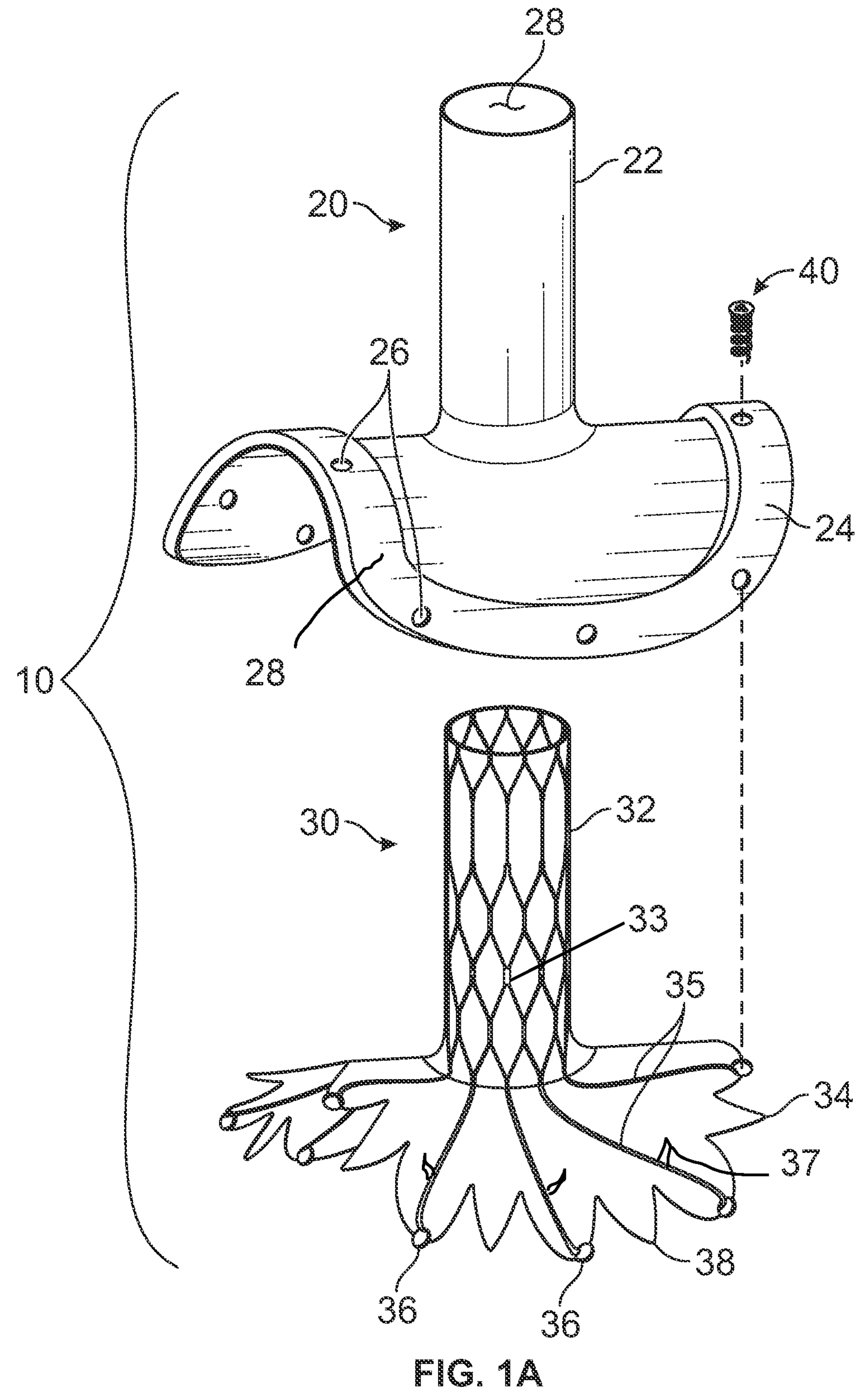
FIG. 1A is a perspective exploded view of an end-to-side anastomosis assembly in accordance with the present disclosure.

For purposes of clarity, the following terms used in this patent application will have the following meanings:

The terminology used herein is for the purpose of describing example embodiments only and is not intended to be limiting. As used herein, the singular forms "a," "an," and "the" may be intended to include the plural forms as well, unless the context clearly indicates otherwise. The terms "comprises," "comprising," "including." and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the order discussed or illustrated, unless specifically identified as an order of performance. It is also to be understood that additional or alternative steps may be employed.

When an element or layer is referred to as being "on," "engaged," "connected," or "coupled" to or with another element, it may be directly on, engaged, connected or coupled to the other element or layer, or intervening elements or layers may be present. In contrast, when an element is referred to as being "directly on," "directly engaged to," "directly connected to," or "directly coupled to" or with another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above." "upper." and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below", or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly "Substantially" is intended to mean a quantity, property, or value that is present to a great or significant extent and less than, more than or equal to total. For example, "substantially vertical" may be less than, greater than, or equal to completely vertical.

"About" is intended to mean a quantity, property, or value that is present at ±10%. Throughout this disclosure, the numerical values represent approximate measures or limits to ranges to encompass minor deviations from the given values and embodiments having about the value mentioned as well as those having exactly the value mentioned. Other than in the working examples provided at the end of the detailed description, all numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. In addition, disclosure of ranges includes disclosure of all values and further divided ranges within the entire range, including endpoints given for the ranges.

The use of the terms "a" and "an" and "the" and similar referents in the context of describing the invention are to be construed to cover both the singular and the plural, unless otherwise indicated herein or clearly contradicted by context. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Recitation of ranges of values herein are merely intended to serve as a shorthand method of referring individually to each separate value falling within the recited range, unless otherwise indicated herein, and each separate value is incorporated into the specification as if it were individually recited herein.

References to "embodiment" or "variant", e.g., "one embodiment," "an embodiment," "example embodiment," "various embodiments," etc., may indicate that the embodiment(s) or variant(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment or variant, although they may.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

The terms "proximal" or "distal" are intended to be relative positional references and are used with reference either to a direction of blood flow relative to a device or device component or with reference to a longitudinal axis of a device or device component. For example, with reference to the graft component, the proximal end of the graft component furthest away from the major vessel or anatomic passageway, whereas the distal end of the graft is the end closest to the major vessel or anatomic passageway.

The term "saddle-shape" when used in connection with an element is intended to mean a generally hyperbolic paraboloid structure.

The term "graft" is intended to refer to any type of polymeric, biological, composite or metal tubular structure.

The term "anatomic passageway" is intended to refer to any anatomical structure having a lumen. Examples of anatomic passageways are blood vessels, the gastrointestinal track, including the esophagus, stomach, small intestine, large intestine, and rectum, or airway passages, such as the trachea and bronchi.

The terms "major vessel" and/or "aorta" as used herein reference specific and non-limiting examples of anatomic passageways. It is intended that the terms "anatomic passageway," "major vessel," and/or "aorta" are used interchangeably and synonymously.

The term "flange" is intended to refer to any type of radially extending projection, including, without limitation, a projection that extends less than or equal to 360 degrees relative to the element that the projection extends from. Further, a flange may have a longitudinal component to its projection orientation relative to the element that the projection extends from.

This detailed description of exemplary embodiments references the accompanying drawings, which show exemplary embodiments by way of illustration. While these exemplary embodiments are described in sufficient detail to enable those skilled in the art to practice the disclosure, it should be understood that other embodiments may be realized and that logical changes and adaptations in design and construction may be made in accordance with this disclosure and the teachings herein without departing from the spirit and scope of the disclosure. Thus, the detailed description herein is presented for purposes of illustration only and not for purposes of limitation.

The accompanying Figures illustrate various embodiments of the end-to-side anastomosis assembly, starting with assembly 10 (hereinafter "assembly 10"). Assembly 10 includes a graft component 20, an affixation component 30 and an attachment component 40. Generally, assembly 10 is configured such that the affixation component 30 is configured to be placed over a guidewire and into a major vessel and abut against a luminal wall surface of the major vessel.

The affixation component 30 is a diametrically expandable stent-like structure and has a proximal portion 32 that is configured to project through the wall of and out of the major vessel and a distal portion 34 that is configured to reside within the lumen of the anatomical passageway. The proximal portion of the affixation component 30 is a tubular proximal section 32 and the distal portion of the affixation component 30 is a radially projecting flange 34 configured to abut and conform to the curvature of the luminal wall surface of the anatomic passageway. To achieve conformation to the curvature of the luminal wall of the anatomic passageway, the radially projecting flange 34 may be configured to assume a generally saddle-shape, such as by shape setting a shape-memory or elastic material of the radially projecting flange 34. Both the tubular proximal portion 32 and radially projecting flange 34 are configured to diametrically expand as the affixation component 30 is deployed from a delivery catheter within the lumen of the major vessel.

The radially projecting flange 34 may, for example, be configured to have a plurality of radially projecting struts 35 extending from a distal end of the tubular proximal section 32 and, optionally, have at least one interconnecting strut 38 that extends circumferentially about the radially projecting flange 34 connecting each of the plurality of radially projecting struts 35. At least one receiver openings 36 is disposed along a length of at least some of the plurality of radially projecting struts 35 and circumferentially arrayed about the radially projecting flange 34. Each receiver openings 36 is configured to receive and engage with an attachment component 40 there through.

The tubular proximal section 32 may be configured with a lattice geometry as is conventional with any of the large number of conventional intraluminal stents, with the proviso that a distal end of the tubular proximal section 32 is configured be contiguous with the radially projecting flange 34 and its structural members and a proximal end of the tubular proximal section 32 is open and in communication with a fluid flow lumen through the tubular proximal section 32 to the distal flanged section 34.

Optionally, a plurality of proximally projecting barbs 37 are provided on at least some of the radially projecting struts 35, at least some of the receiver openings 36 and/or along the interconnecting strut 38. The barbs 37 are configured to penetrate into the luminal wall surface of the major vessel and secure the affixation component 30 against the luminal wall surface such that the affixation component 30 does not rotate about its longitudinal axis or dislodge from abutment with the luminal wall surface of the anatomic passageway.

Once properly positioned in the major vessel, the radially projecting flange 34 may be further approximated against the luminal wall surface of the major vessel affixation component 30 such as by expanding a balloon within the lumen of the major vessel against the luminal facing surface of the radially projecting flange 34.

Figure 1B:
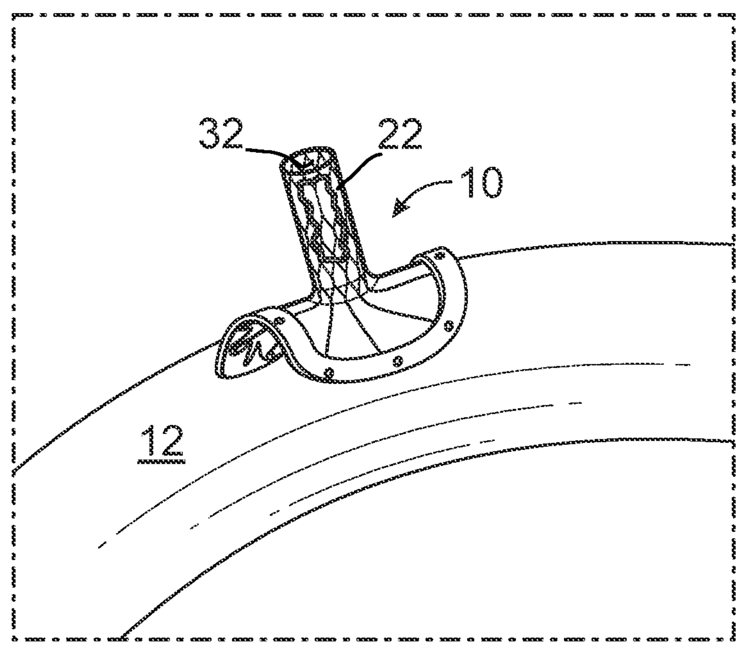
FIG. 1B is a perspective view of a variant of an end-to-side anastomosis assembly approximated with an anatomic passageway in accordance with the present disclosure.

Once the affixation component 30 is positioned and secured in the lumen of the anatomic passageway, such as a major blood vessel, the graft component 20 is then introduced and placed concentrically over the tubular portion 32 of the affixation component 30. In one variant as illustrated in FIG. 1, the graft component 20 has a proximal tubular graft section 22 and a distal flange section 24. A plurality of receiver openings indicators 26 are provided about the periphery of the distal flange section 24, receiver openings indicators 26 may be visual positional indicia on the surface of the distal flange section or, alternatively or in addition, openings passing through the distal flange section 24 that accommodate passing tissue anchors from the anchoring component 40 there through, as is discussed in greater detail infra. When the graft component 20 is engaged with the affixation component 30, at least some of the plurality of receiver openings indicators 26 will be positioned in axial alignment with one of the plurality of receiver openings 36 on the radially projecting flange 34 of the affixation component 30.

The distal flange section 24 is contiguous with the tubular portion 22 and projects radially outward from the distal end of the tubular portion 22. As previously discussed, the distal flange section 24 will have a shape that conforms to the curvature of an abluminal wall surface of the anatomic passageway and may be configured to have a substantially saddle-shape to accomplish close abutment with the abluminal wall surface of the anatomic passageway. The distal flange section 24 may, optionally, have a reinforcing section 28, which may be a thickened portion of the distal flange section 24, a reinforced portion of the distal flange section 24, such as by incorporating a stiffer material into the distal flange section 24, or may be a separate annular structure that overlies the distal flange section 24. In each case the reinforcing section 28 preferably extends circumferentially about the periphery of the distal flange section 24. Reinforcing section 28 may be unitary or segmented. When provided, the plurality of receiver openings 26 may be positioned to pass through the reinforcing section 28 of distal flange section 24 of the graft component 20.

The graft component 20, including the proximal tubular graft section 22 and/or the distal flange section 24, may have, in whole or in part, a graft reinforcement that serves as a support structure for the graft component 20. An example of flanged graft is illustrated in U.S. Pat. No. 6,652,578, which is hereby incorporated by reference in its entirety, teaching a cardiac valve stent having a stent-like support structure with an anchoring flange and a DACRON or expanded polytetrafluoroethylene ("PTFE") graft supported on either or both of a luminal or abluminal surface surfaces or the stent-like support structure. The graft component 20 may be made of DACRON, PTFE, or other suitable biocompatible polymeric material, biocompatible composite materials, biological material, biocompatible metals, or combinations thereof. PTFE grafts having an enlarged or flanged skirt for end-to-side anastomosis, and methods of making the same are exemplified by U.S. Pat. Nos. 6,190,590, 6,203,735 and/or 9,445,886, each of which is incorporated by reference.

A plurality of anchoring components 40 are provided to affix the graft component 20 to the affixation component 30 through the wall of the major vessel 12. The anchoring components 40 may be tissue screws, pins, retainers, clips, staples, or the like, provided that each of the plurality of anchoring components act to engage with the receiver openings 36 in the affixation component 30 through the graft component 20 and the major vessel wall 12.

Figure 2:
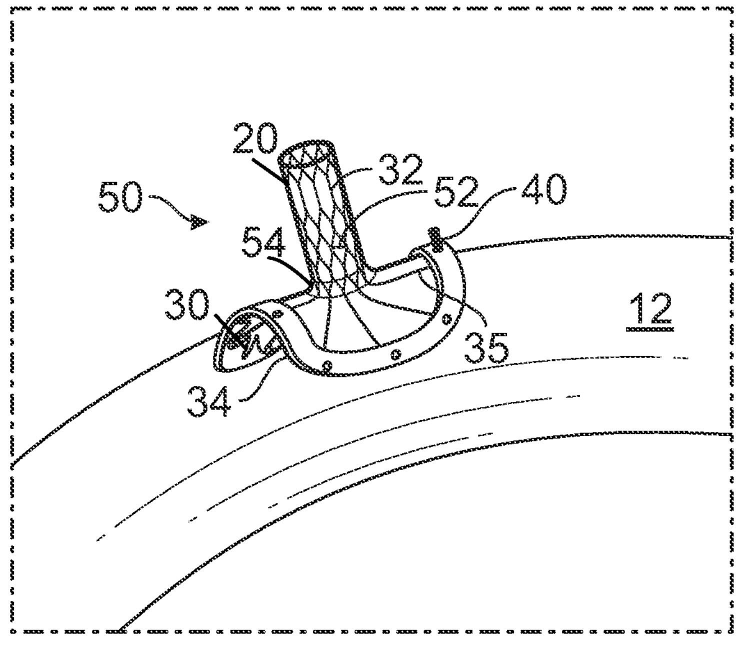
FIG. 2 a perspective view of an end-to-side anastomosis assembly fragmentary perspective view of the end-to-side anastomosis assembly showing a tissue anchoring component engaged with the end-to-side anastomosis assembly to an anatomic passageway.
Figure 3:
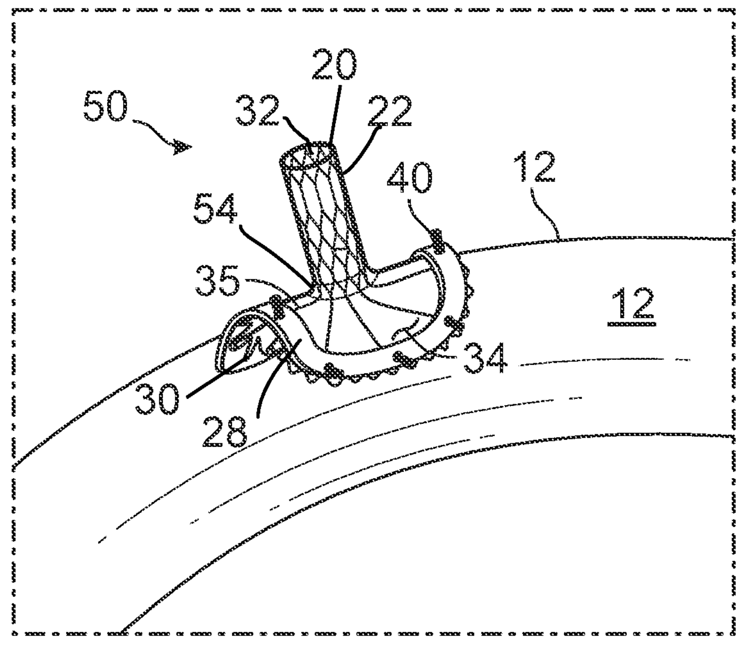
FIG. 3 is a perspective view of an end-to-side anastomosis assembly fragmentary perspective view of the end-to-side anastomosis assembly showing tissue anchoring components affixing the end-to-side anastomosis assembly to an anatomic passageway.

A variant of the end-to-side anastomosis assembly 50 (hereinafter "assembly 50") is shown in FIG. 2 and FIG. 3. In assembly 50 the graft component 20 is integrated with the tubular portion 32 of the affixation component 30 and with respect to this variant is referred to as the "integral graft component 20." In this variant, integral graft component 20 has only a proximal tubular graft section 52, which is similar to the tubular proximal section 22, that extends from a proximal end of the affixation component 30 and has a distal tubular graft section 54 that terminates at or proximate to the distal end of the proximal tubular section 52 of the affixation component 30. The graft component 52, in this variant, does not have a distal flange section 24 as in assembly 10. In this variant, the plurality of anchoring components 40 may pass directly into a reinforcing section 28 or axial compression plate(s) 70 (shown in FIG. 4B) and through the major vessel wall 12 and engage with the receiver openings 36 on the distal flange 34 of the affixation component 30. Optionally, to facilitate positioning of the anchoring components 40 through the major vessel wall 12, the receiver openings 36 may each have at least one of a plurality of barbs 37 (shown in FIG. 1 and a common optional element to all embodiments described herein) that have a length configured to pass into and through the major vessel 12 wall to allow the surgeon to visualize the position of the receiver openings 36 through the major vessel 12 abluminal wall surface. When provided, the plurality of barbs 37 add further mechanical affixation to the luminal wall of the anatomic passageway and additional positional stabilization of the affixation component 30 to resist migration within the anatomic passageway.

The integral graft component 20 may be on the luminal and/or abluminal wall surfaces of the tubular portion of the affixation component 30 and secured to either the tubular portion 32 or to each other through interstices of the affixation component 30. The proximal tubular section 22 of the integral graft component 20 will have a proximal section and extending toward the intersection with the distal section to facilitate achieving a hemostatic seal with the aorta. In this optional configuration, the integral graft component 20 integrated with the tubular proximal section 32 of the affixation component 30 may obviate the need for a graft component 20 that is discrete or separate from the affixation component 30 and must be joined thereto during a procedure. An example of an integrated graft with a stent is found at U.S. Pat. No. 5,749,880 ("the '880 Patent") which discloses an ePTFE covering on both the luminal and abluminal surfaces of a stent and encapsulating the stent through interstices in the stent. The '880 Patent is hereby incorporated by reference in its entirety as if fully set forth herein.

Figure 4A:
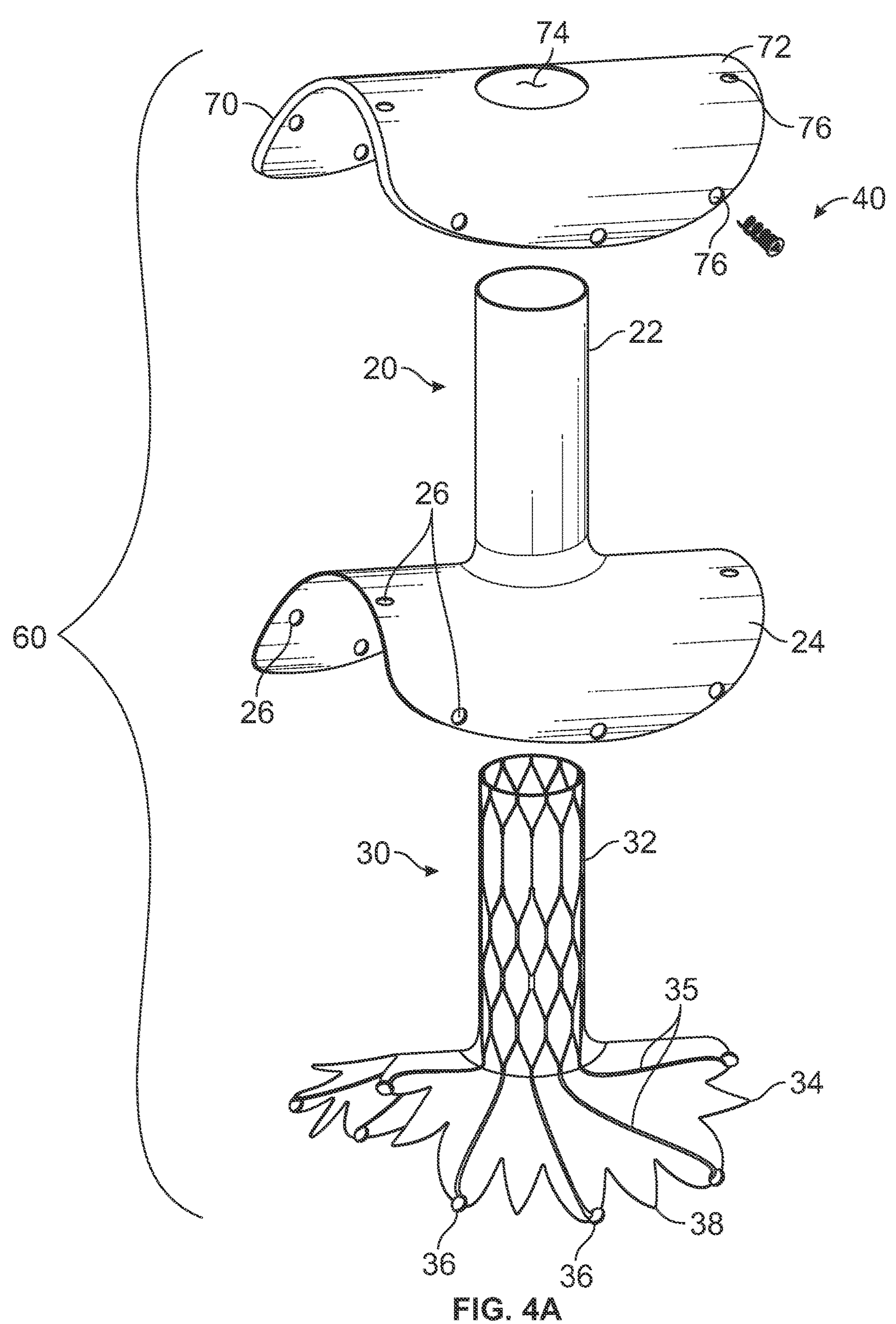
FIG. 4A is a perspective exploded view of an alternative end-to-side anastomosis assembly in accordance with the present disclosure.
Figure 4B:
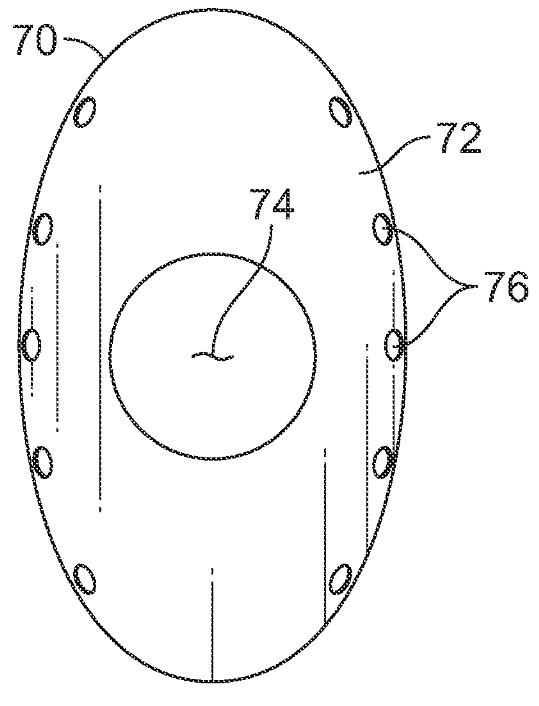
FIG. 4B is a top elevational view of compression plate in accordance with the alternative end-to-side anastomosis assembly in accordance with the present disclosure.
Figure 4C:
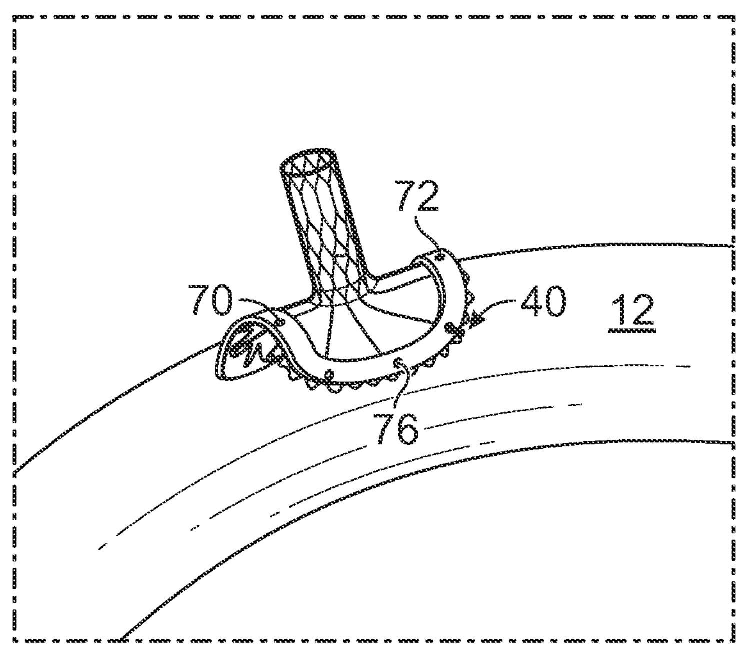
FIG. 4C is a perspective view of the alternative end-to-side anastomosis assembly approximated with an anatomic passageway.

Turning now to FIGS. 4A-4C, there is shown an alternative embodiment of end-to-side anastomosis assembly 60 (hereinafter "assembly 60) that includes an axial compression plate 70 having a central annular opening 74 and a plate body 72. The plate body 72 is configured to conform to the curvature of an abluminal wall surface of an anatomic passageway and may have a pre-determined or pre-formed substantially saddle-shape that is configured to conform to the abluminal wall curvature. A plurality of openings 76 are arrayed about the circumference of the plate body 72. Openings 76 are configured to allow the anchoring components 40 to pass into and through the plate body 72 to secure the axial compression ring to the distal flange 24 of the graft component and/or to the receiver openings 36 of the distal flange 34 of the affixation component 30.

The plate body 72 may be a unitary member of segmented members that cooperate to form the plate body 72. The axial compression plate 70 is configured to nest with the graft component 20 and/or the affixation component 30. When the assembly 60 is delivered to a major vessel, the affixation component 30 and graft component 20 are delivered and positioned relative to the major vessel as described, supra, with respect to assembly 10. However, in assembly 60, the anchoring component 40, e.g., tissue anchors, are not placed directly into the receiver openings indicators 26. Rather, the axial compression plate 70 is placed over the proximal tubular graft section 22 of the graft component 20 such that the proximal tubular graft section 22 passes into and through the central opening 74 of the axial compression plate 70 and the plate body 72 is nested onto the distal flange section 24 of the graft component 20, onto the reinforcing section 28, or directly onto the abluminal wall surface of the anatomic passageway. In this manner, the axial compression plate(s) 70, the distal flange section 24 of the graft component 20, and/or the distal flange 34 of the affixation component 30 are then nested to each other and to the abluminal wall of the major vessel 12.

Once the axial compression plate 70 is nested against the graft component 20 and/or the abluminal wall of the major vessel 12, the anchoring component 40 may then be delivered through the plurality of openings 72 in the axial compression plate 70, into and through the receiver openings indicators 26 of the graft component, through the wall of the major vessel 12, and into and engaging with the receiver openings 36 of the affixation component 30. Once engaged with the receiver openings 36, the anchoring components 40 bear against both the axial compression plate 70 and the receiver openings 36 of the affixation component 30 to draw the assembly together against both the abluminal and luminal wall surfaces of the major vessel 12.

Figure 5:
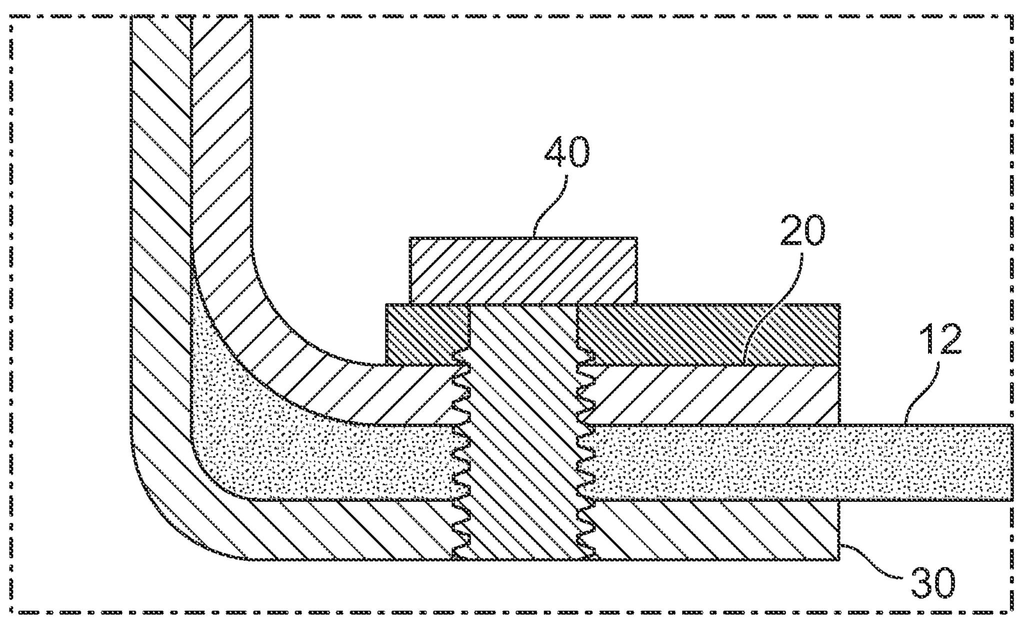
FIG. 5 is a side cross-sectional fragmentary view illustrating tissue anchor affixation passing through a distal flange portion of a graft component, anatomic tissue, and engaged with a distal flange portion of the affixation component of the end-to-side anastomosis assembly of the present disclosure.
Figure 6:
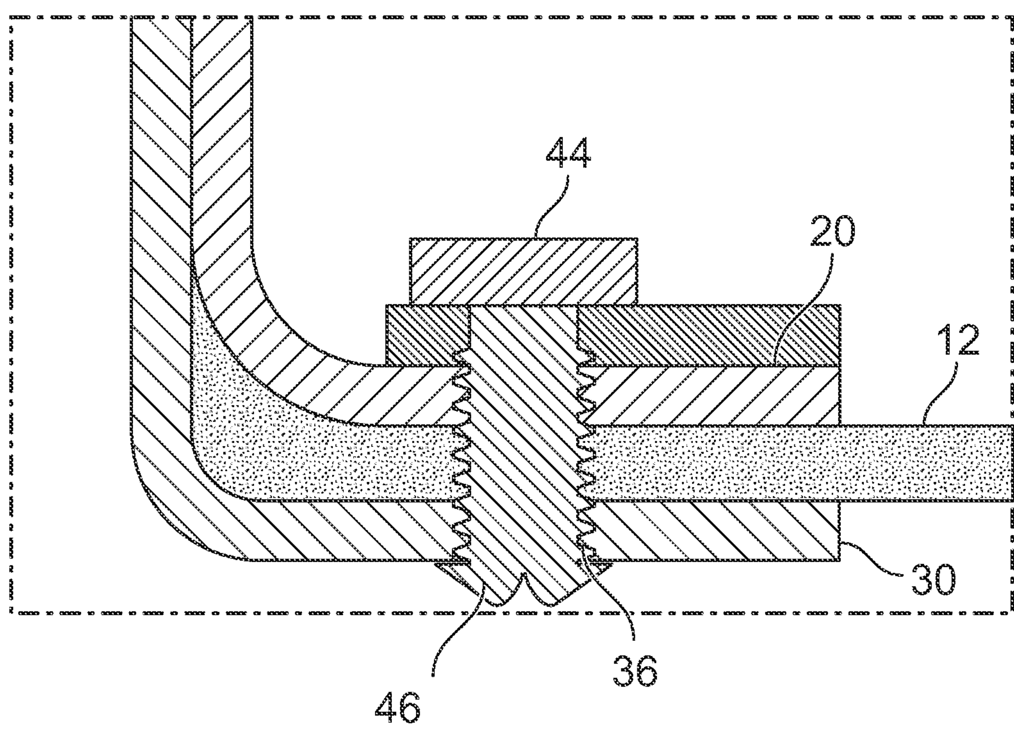
FIG. 6 is a side cross-sectional fragmentary view illustrating an alternative tissue anchor affixation passing through the distal flange portion of the graft component, the anatomic tissue, and engaged with the distal flange portion of the affixation component of the end-to-side anastomosis assembly of the present disclosure.

FIGS. 5 and 6 illustrate the two different embodiments of the anchoring component 40 and assembly 10 delivered and capturing a major vessel between the graft component 20 and the affixation component 30 under the influence of axial compression exerted by the anchoring component 40. In FIG. 5, the anchoring component 40 is a tissue screw 42 having a tissue screw head and a helical coil projecting from the tissue screw head, the tissue screw having a length that terminates in close proximity to the luminal wall surface of the affixation component. In FIG. 6, the anchoring component 40 is an expandable pin 44, having a pin head that bears against graft component 20 and an expandable pin end 46 opposite the pin head that diametrically expands once inserted through the receiver openings 36 to fix the expandable pin 44 in the receiver openings 36. It will be understood that while FIGS. 5 and 6 omit the axial compression plate 70, that the same configuration of anchoring components 40 may be employed with assembly 60 such that the tissue screw head or pin head bears against the axial compression plate 70 and passes through the axial compression plate, the graft component 20, the major vessel 12, and the receiver openings 36 of the affixation component 30.

It will be appreciated by those skilled in the art, that when the major vessel 12 is opened, such as by coring or dilation, there are always risks of vessel dissection or hematoma formation between the vascular tissue layers. Both of these risks are mitigated by isolating and compressing the vascular tissue between the graft component 20 and the affixation component 30 which are secured to each other by tissue anchor 40, which substantially reduces the potential for vessel wall injury.

Figure 7:
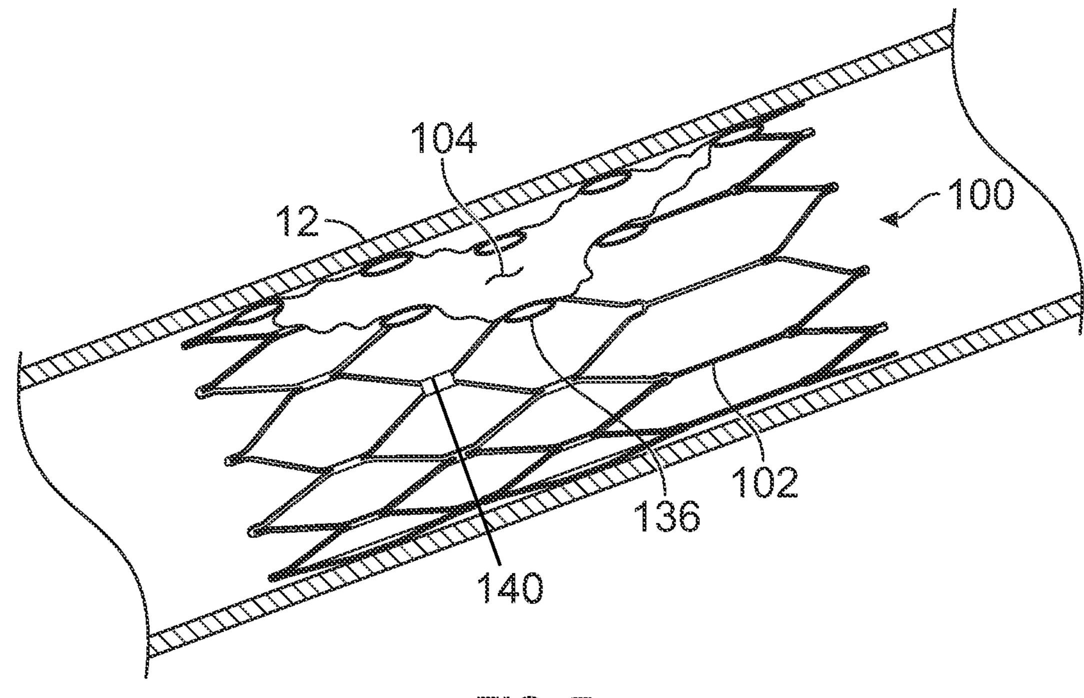
FIG. 7 is a perspective view of an alternative stent-like affixation component of the end-to-side anastomosis assembly in accordance with the present disclosure.

FIG. 7 is an alternative embodiment of the end-to-side anastomosis assembly 100 (hereinafter "assembly 100"). Assembly 100 includes a tubular stent-like frame 102 that is diametrically expandable from a first reduced diameter delivery state to a second expanded diameter state within the lumen of an anatomic passageway 12. The tubular stent-like frame 102 may have a sensor 140 either coupled to or integrated therewith. Sensor 140 may operate to sense any of a wide variety of physiological conditions within the major vessel 12 based upon blood flow through the tubular stent-like frame 102 and communicate data pertaining to such physiological conditions wireless to a receiver or transceiver external to the patient's body. Similar sensor(s) 33 may also be placed on the proximal tubular portion 32 of the affixation component 30, as shown in FIG. 1A, or on the distal section thereof, to sense a physiological condition within the affixation component. The tubular stent like frame 102 has a generally annular shaped opening 104 in a side wall thereof. A plurality of receiver openings 136 are provided in the tubular stent frame and about the periphery of the opening 104. The assembly 100 is delivered by intraluminal access to a site in a major vessel and is configured to be placed within the major vessel. Either concurrently, or later in time, the major vessel 12 may be accessed, such as by transthoracic access, to place the graft component 20, the anchoring component 40, and, optionally, the axial compression plate 70 onto the abluminal wall surface of the major vessel and positioned in axial alignment with the opening 104 in assembly 100, such that the anchoring component secures the graft component 20 and, optionally, the axial compression plate 70, to the receiver openings 135 in assembly 100, through the wall of the major vessel 12. Once positioned and secured with the anchoring components, the graft component 20, optionally, the axial compression plate 70, and the assembly 100, the portion of the major vessel 12 exposed within the area of the opening 104 and through the tubular graft proximal section 22 may be then cored to allow blood flow into and through the tubular graft proximal section 22 and into the major vessel through the assembly 100. Balloon occlusion proximal or upstream from the tubular stent-like frame 102 will support the vessel and prevent the flow of blood into the tubular stent-like frame 102 and facilitate connection of the graft component 20 through the vessel wall under both low pressure and low or no blood flow conditions.

Once assembly 10, assembly 50, assembly 60, or assembly 100 are placed with respect to an anatomic passageway 12, such as a major vessel, the output from a tubular conduit, such as from a VAD pump or other fluid source, is coupled to the proximal tubular graft section 22 and the tubular proximal section 32 of the affixation component 30. It will be understood that the output tubular conduit may, itself, be an anatomic passageway or may be an exogenous conduit such as a surgical graft. The output tubular conduit may be concentrically joined about the proximal graft section 22 and securing it in a hemostatic manner by any of a wide variety of hemostatic securements. Examples of suitable hemostatic securements include, for example, a suture ligature, a circumferential cinch, a circumferential clamp, barb fittings, or other hemostatic fittings, or the like. It is important, however, that the hemostatic securement does not constrict or impede patency of the lumen within the proximal tubular graft section 22 and the tubular proximal section 21 of the affixation component 30.

It will be understood that the various embodiments described of the graft component, the affixation component, the anchoring component, the axial compression plate with respect to assembly 10, assembly 50, and/or assembly 60 may be interchangeable with one another. For example, the graft component 20 in assembly 10 may be substituted with an affixation component having an integrated or attached graft component 52 from assembly 50. Similarly, the reinforcing ring 35 in assembly 50 may be employed as the reinforced peripheral section 28 in assembly 10 or added to assembly 60 as additional reinforcement for the distal flange 24 of graft component 20. Further, the axial compression plate(s) 70 may be employed with the graft component 20 in any of the assemblies 10, 50, or 100. Accordingly, the embodiments are not intended to be limited to the specific embodiments depicted in the accompanying Figures but may exchange or substitute components from other embodiments of assembly 10, assembly 50, assembly 60, and/or assembly 100.

As noted above, the variants of end-to-side anastomosis assembly 10, 60, and/or 100 may also be used in a wide variety of non-vascular medical applications to create end-to-side conduits between anatomic passageways or between a tubular conduit and an anatomic passageway. Those skilled in the art will appreciate and understand that the scope of utility and the scope of the constructs of the end-to-side assemblies of the present disclosure described herein may have a large number of variations and that the scope of the invention is limited only by the claims appended hereto.

The invention claimed is:

1. An assembly configured for end-to-side anastomosis, comprising, in combination a graft component having a tubular proximal section and a distal flange section, an affixation component comprising a diametrically expandable proximal tubular section and a diametrically expandable distal flange section, the diametrically expandable distal flange section comprising a plurality of radially extending strut members and at least one circumferential strut member connecting each of the plurality of radially extending strut members, wherein the diametrically expandable distal flange section is configured to conform to a luminal wall surface of an anatomic passageway; a plurality of receiver openings are arrayed about the distal flange section and positioned at a juncture between at least one of the plurality of radially extending strut members and the at least one circumferential strut member; wherein the affixation component is configured to at least partially be placed within an anatomic passageway and conform to a luminal wall surface of the anatomic passageway, the affixation component having a plurality of receiver openings therein, a plurality of tissue anchors configured to pass through the distal flange section of the graft component, pass into and through a wall of the anatomic passageway, and engage with the plurality of receiver openings in the affixation component; and an axial compression plate having a central annular opening configured to receive the tubular proximal section of the graft component therethrough and configured to conform to and bear against the distal flange section of the graft component, the axial compression plate having a plurality of openings passing therethrough and positioned about the axial compression plate, each of the plurality of openings being in axial alignment with one of the plurality of receiver openings in the distal flange section of the affixation component.

2. The assembly of claim 1, wherein the distal flange section of the graft component is configured to conform to curvatures of an abluminal wall surface of the anatomical passageway.

3. The assembly of claim 2, wherein the distal flange section of the affixation component is configured to conform to curvatures of the luminal wall surface of the anatomical passageway.

4. The assembly of claim 1, wherein the plurality of tissue anchors bear against a proximal surface of the distal flange section of the graft component and exert an axially compressive force between the graft component and the affixation component securing the anatomical passageway wall there between.

5. The assembly of claim 1, wherein the affixation component further comprises a diametrically expandable stent having an annular open region in a wall surface thereof, wherein the plurality of receiver openings are circumferentially arrayed about the annular open region.

6. The assembly of claim 1, wherein the affixation component further comprises a plurality of barbs projecting from the affixation component and configured to embed into the anatomical passageway.

7. The assembly of claim 1, wherein at least some of the tissue anchors further comprise tissue screws.

8. The assembly of claim 7, wherein the tissue screws each further comprise a tissue screw head and a helical coil projecting from the tissue screw head, the helical coil being configured to engage with the plurality of receiver openings.

9. The assembly of claim 1, wherein at least some of the tissue anchors further comprise expandable pins.

10. The assembly of claim 9, wherein each of the expandable pins further comprise a pin head and an expandable pin end configured to diametrically expand when the expandable pin is engaged with the plurality of receiver openings.

11. The assembly of claim 1, further comprising at least one sensor configured for sensing a physiological condition within the anatomical passageway, the at least one sensor being coupled with the affixation component.

12. An end-to-side anastomosis assembly, comprising, in combination a graft having a tubular proximal section and a distal flange section, a stent configured to be placed within a lumen of a blood vessel and conform to a luminal wall surface of the blood vessel, the stent having an annular opening in a wall thereof and a plurality of eyelet members each having a receiver opening arrayed about the annular opening; and a plurality of tissue anchors to pass through the distal flange section of the graft component, pass into and through a wall of the blood vessel, and engage with the plurality of receiver openings in the stent, thereby axially compressing the distal flange section, the blood vessel wall, and the stent to each other.

13. The end-to-side anastomosis assembly of claim 12, wherein the distal flange section of the graft component is configured to conform to curvatures of an abluminal wall surface of the blood vessel.

14. The end-to-side anastomosis assembly of claim 12, further comprising an axial compression plate having a central annular opening configured to receive the tubular proximal section of the graft therethrough and is configured to conform to and bear against the distal flange section of the graft.

15. The end-to-side anastomosis assembly of claim 14, wherein the axial compression plate further has a plurality of openings passing through the axial compression plate and positioned about the axial compression plate, each one of the plurality openings being in axial alignment with one of the plurality of receiver openings in the stent, wherein the tissue anchors bear against the axial compression plate and pass through the distal flange section of the graft, the blood vessel wall, and engage with the plurality of receiver openings in the stent.

16. An assembly configured for end-to-side anastomosis, comprising, in combination a graft component having a tubular proximal graft section and a distal flange graft section, an affixation component comprising a diametrically expandable lattice structure defining a proximal tubular affixation section and a distal flange affixation section, the distal flange affixation section having a plurality of eyelets having receiver openings arrayed about a circumference thereof and is configured to conform to a luminal wall surface of an anatomic passageway; wherein the affixation component is configured to be placed within an anatomic passageway such that the proximal tubular section passes through a wall of the anatomic passageway and the distal flange affixation section abuts the luminal wall surface of the anatomic passageway; and a plurality of tissue anchors configured to pass through the distal flange graft section, pass into and through the anatomic passageway, and engage with the plurality of receiver openings in the affixation component and axially compress the anatomic passageway between the distal flange graft section and the distal flange affixation section.

17. The end-to-side anastomosis assembly of claim 16, wherein the distal flange section of the graft component is configured to conform to curvatures of an abluminal wall surface of the anatomic passageway.

18. The end-to-side anastomosis assembly of claim 16, further comprising an axial compression plate having a central annular opening configured to receive the tubular proximal section of the graft therethrough and is configured to conform to and bear against the distal flange graft section.

19. The end-to-side anastomosis assembly of claim 18, wherein the axial compression plate further has a plurality of openings passing through the axial compression plate and positioned about the axial compression plate, each one of the plurality openings being in axial alignment with one of the plurality of receiver openings in the stent, wherein the tissue anchors bear against the axial compression plate and pass through the distal flange graft section, the blood vessel wall, and engage with the plurality of eyelets in the distal flange affixation section.

* * * * *